(12) United States Patent
Yen

(10) Patent No.: US 7,029,566 B2
(45) Date of Patent: Apr. 18, 2006

(54) PROCESS OF FORMING HA/ZRO$_2$ COMPLEX COATING ON CO—CR—MO ALLOY

(75) Inventor: Shiow-Kang Yen, Taichung (TW)

(73) Assignee: Chinese Petroleum Corporation, Taipei City (TW)

( * ) Notice: Subject to any disclaimer, the term of this patent is extended or adjusted under 35 U.S.C. 154(b) by 335 days.

(21) Appl. No.: 10/660,530

(22) Filed: Sep. 12, 2003

(65) Prior Publication Data

US 2005/0056543 A1    Mar. 17, 2005

(51) Int. Cl.
*C25D 5/50* (2006.01)
*C25D 9/04* (2006.01)

(52) U.S. Cl. .............. 205/170; 205/224; 205/318; 205/333

(58) Field of Classification Search ........... 205/170, 205/224, 318, 333
See application file for complete search history.

(56) References Cited

U.S. PATENT DOCUMENTS

| | | | | |
|---|---|---|---|---|
| 5,480,438 | A | * | 1/1996 | Arima et al. ............ 623/23.6 |
| 5,723,038 | A | * | 3/1998 | Scharnweber et al. ...... 205/107 |
| 5,759,376 | A | * | 6/1998 | Teller et al. ............ 205/50 |
| 6,645,644 | B1 | * | 11/2003 | Schwartz et al. .......... 428/632 |
| 2003/0099762 | A1 | * | 5/2003 | Zhang et al. ............ 427/2.1 |

* cited by examiner

*Primary Examiner*—Roy King
*Assistant Examiner*—William T. Leader
(74) *Attorney, Agent, or Firm*—Troxell Law Office, PLLC

(57) ABSTRACT

In a process of forming a HA/ZrO$_2$ complex coating on a Co—Cr—Mo alloy substrate, the substrate is subjected to electrolytic deposition respectively in a ZrO(NO$_3$)$_2$ bath and a mixed solution of Ca(NO$_3$)$_2$.4H$_2$O and NH$_4$H$_2$PO$_4$ to respectively form Zr(OH)$_4$ colloidal layer and Ca$_{10}$(PO$_4$)$_6$(OH)$_2$ layer. Then, the substrate is subjected to a low-temperature sintering process to convert the two layers into a HA/ZrO$_2$ complex coating.

39 Claims, 2 Drawing Sheets

PROCESS OF FORMING HA/ZRO$_2$ COMPLEX COATING ON CO—CR—MO ALLOY

BACKGROUND OF THE INVENTION

1. Field of the Invention

The invention relates to a process of forming a process of forming a HA/ZrO$_2$ complex coating on a metallic surface, and more particular, to a process of forming a HA/ZrO$_2$ bio-ceramic coating on a Co—Cr—Mo alloy by electrolytic deposition.

2. Description of the Related Art

An artificial articulation coxa includes a femoral stem, a femoral head and an acetabular cup. The major movement of the articulation coxa occurs between the femoral head and the acetabular cup. Therefore, corrosion made by the relative movement of the femoral head and the acetabular cup greatly affects the service life of the artificial articulation coxa. Co—Cr—Mo alloy is well used as the material of the articulation coxa due to its advantages of high mechanical strength and good toughness. However, the Co—Cr—Mo alloy is easily corroded to release toxic ions if stayed in human's body fluid for a long time. This problem can be solved by various surface modifications including hot isostatic pressing, plasma or flame spraying, ion-beam sputtering deposition, elelctrophoretic deposition, sol-gel deposition and radio-frequency magnetron sputtering.

ZrO$_2$ is a ceramic material with high corrosion resistance, chemical stability and bio-compatible ability. One of the surface modifications utilizes the characteristic of ZrO$_2$ to inhibit toxic ion release from the Co—Cr—Mo alloy and to prevent the corrosion of the Co—Cr—Mo alloy. For example, TW patent No. 138232 discloses ZrO$_2$ has good adhesion to the Co—Cr—Mo alloy, and the ZrO$_2$-coated Co—Cr—Mo alloy has very good corrosion resistance.

The bioactivity and bio-compatibility of Ca$_{10}$(PO4)$_6$(OH)$_2$ (HA) has been proved. However, applications of the HA are limited due to its disadvantageously poor mechanical. At present, the HA is clinically applied to only non-load-bearing area. If the mechanical strength of HA can be improved, its applications must to be greatly extended, such as in use as the artificial articulation coxa.

The inventors have found that the combination of ZrO$_2$ and HA increases the bioactivity of Co—Cr—Mo alloy as well as the mechanical strength and adhesion of HA, to improve the performance of the artificial coxa.

Furthermore, the ZrO$_2$ and HA have to be sintered at a temperature higher than 500° C., which requires high thermal budget. High-temperature sintering always results in phase change of final products, for example, the heterophase of the obtained coating, such as DCP or β-TCP.

Therefore, there is a need of a high-quality surface modification on the Co—Cr—Mo alloy with low thermal budget, and of a highly surface modified Co—Cr—Mo alloy.

SUMMARY OF THE INVENTION

It is therefore a principal object of the invention to provide a process of forming a HA/ZrO$_2$ complex coating on a Co—Cr—Mo alloy substrate that is used to form an artificial articulation coax, in which the HA/ZrO$_2$ complex coating prevents any ions harmful to the organism from being released from the Co—Cr—Mo alloy substrate and increases the mechanical strength of the artificial articulation coax.

It is another object of the invention to provide a process of forming a HA/ZrO$_2$ complex coating on a Co—Cr—Mo alloy substrate, in which the HA/ZrO$_2$ complex coating having high bioactivity and mechanical strength.

In order to achieve the above and other objectives, the process of forming a HA/ZrO$_2$ complex coating on a Co—Cr—Mo alloy substrate includes two electrolytic deposition steps to form Zr(OH)$_4$ colloidal layer and Ca$_{10}$(PO$_4$)$_6$(OH)$_2$ layer respectively using ZrO(NO$_3$)$_2$ bath and a mixed solution of Ca(NO$_3$)$_2$.4H$_2$O and NH$_4$H$_2$PO$_4$. These layers are subjected to a low temperature sintering process to form a HA/ZrO$_2$ complex coating.

In the invention, the Co—Cr—Mo alloy substrate is placed in ZrO(NO$_3$)$_2$ bath and subjected to electrolytic deposition. Then, the ZrO(NO$_3$)$_2$-coated Co—Cr—Mo alloy substrate is moved to a mixed solution of Ca(NO$_3$)$_2$.4H$_2$O and NH$_4$H$_2$PO$_4$ from the ZrO(NO$_3$)$_2$ bath and subjected to electrolytic deposition. Thereafter, the substrate is dried very slowly to remove most of moisture from these coatings in order to prevent any crack generated during the later sintering process. Then, the sintering process is performed at no more than 500° C. to form the HA/ZrO$_2$ complex coating on the Co—Cr—Mo alloy substrate. The sintering temperature is raised at several stages to prevent delamination of the coating.

With the process of the invention, the bioactivity of the Co—Cr—Mo alloy substrate increases, and the mechanical strength and adhesion of HA increase as well. The inherent advantages of the HA and ZrO$_2$ themselves are combined to improve the performance in medical applications.

BRIEF DESCRIPTION OF THE DRAWINGS

The drawings included herein provide a further understanding of the invention. A brief introduction of the drawings is as follows.

DETAILED DESCRIPTION OF THE EMBODIMENTS

Figure 1:
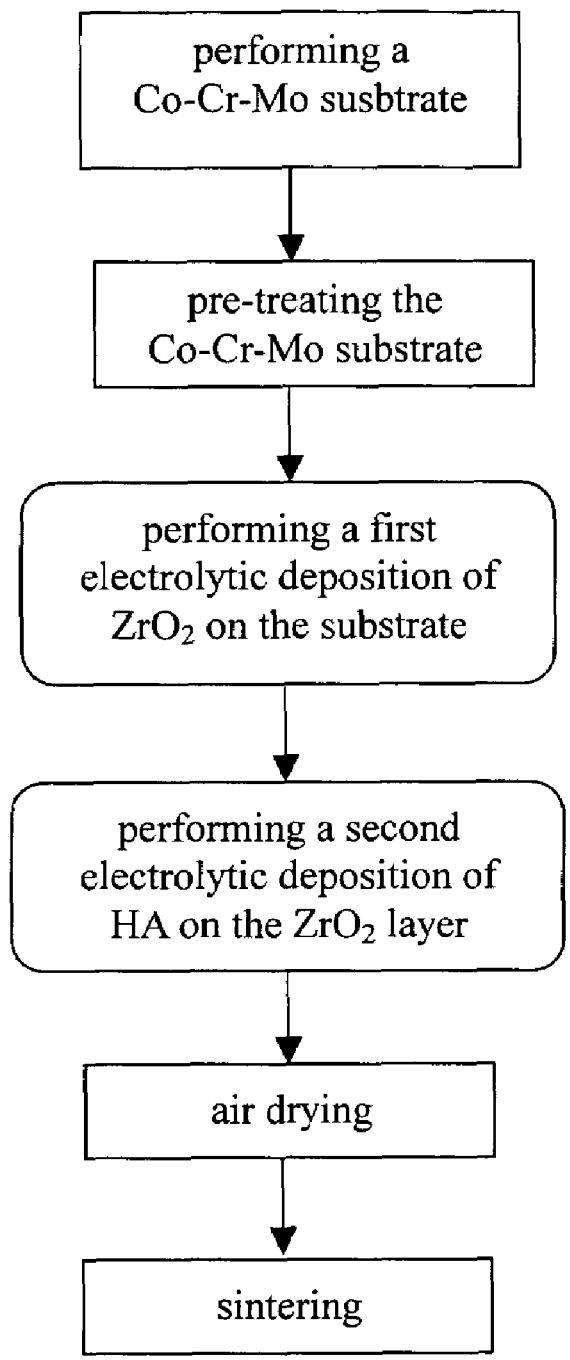
FIG. 1 is a flow chart illustrating a process of forming HA/ZrO$_2$ complex coating according to one embodiment of the invention.

FIG. 1 is a flow chart illustrating a process of forming HA/ZrO$_2$ complex coating according to one embodiment of the invention. Although the invention is illustrated by using a Co—Cr—Mo alloy substrate as a substrate, the Ha/ZrO$_2$ complex coating is also able to form on other substrate.

The process of forming a HA/ZrO$_2$ complex coating on a Co—Cr—Mo alloy substrate according to the invention is characterized by two electrolytic deposition steps respectively using ZrO(NO$_3$)$_2$ bath and a mixed solution of Ca(NO$_3$)$_2$.4H$_2$O and NH$_4$H$_2$PO$_4$.to Zr(OH)$_4$ and Ca$_{10}$(PO$_4$)$_6$ (OH)$_2$ on the Co—Cr—Mo alloy susbtrate. The description of the process is described in detail as follows.

First, the Co—Cr—Mo alloy substrate is placed in ZrO(NO$_3$)$_2$ bath and subjected to a first electrolytic deposition. The first electrolytic reaction mechanism is as follows:

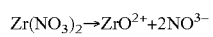

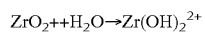

$$H_2O + 2e^- \rightarrow H_2 + 2OH^-$$

$$Zr(OH)_2^{2+} + 2OH^- \rightarrow Zr(OH)_4$$

After the first electrolytic reaction is completed, a $Zr(OH)_4$ colloidal layer is formed on the Co—Cr—Mo alloy substrate. Then, the Co—Cr—Mo substrate is moved to a mixed solution of $Ca(NO_3)_2 \cdot 4H_2O$ and $NH_4H_2PO_4$ from the $ZrO(NO_3)_2$ bath to be subjected to a second electrolytic deposition. The second electrolytic deposition is as follows:

$$Ca(NO_3)_2 + Ca^{2+} + 2NO^{3-}$$

$$2HPO_4^{2-} + 2e^- \rightarrow 2PO_4^{3-} + H_2$$

$$2H_2O + 2e^- H_2 + 2OH^-$$

$$10Ca^{2+} + 6PO_4^{3-} + 2OH^- \rightarrow Ca_{10}(PO_4)_6(OH)_2$$

After the second electrolytic reaction, a $Ca_{10}(PO_4)_6(OH)_2$ layer is formed on the $Zr(OH)_4$ colloidal layer. Then, the substrate is subjected to slow drying and low temperature sintering to convert the two layers into a $HA/ZrO_2$ complex coating. The sintering temperature is not higher than 500° C.

The inventors have found that deposition voltage, deposition time and electroplating solution are crucial to the quality of a film formed by electrolytic deposition. These three factors are discussed in detail as follows.

The deposition voltage greatly affects the adhesion of HA onto the $ZrO_2$. At the $ZrO_2$ forming step, the voltage ranges from −0.6V~−2.5V, preferably from −0.75V~−1.1V. At the HA forming step, the voltage ranges from −0.5V~−3V, preferably from −0.6V~−1.4V. The above voltage range is determined relative to the voltage of a mercurous chloride reference electrode.

The coating obtained with the voltage of the above range has improved adhesion and no delamination occurs. When the voltage is larger than the up limit of the above range, bubbles easily adhere onto the substrate, which results in low density of the HA layer. When the voltage is smaller than the low limit range of the above range, the HA layer is not uniform.

Proper deposition time not only increases the uniformity and density of the coating, but also increases the deposition efficiency. The topography of the $Zr(OH)_4$ layer may affect the deposition of HA. If the deposition time is too short, the HA layer may not uniformly cover the $Zr(OH)_4$ layer. If the deposition time is too long, the HA layer may delaminate from the $Zr(OH)_4$ layer. At the $ZrO_2$ forming step, the deposition time ranges from 150 s~3500 s, and preferably from 300 s~2000 s. At the HA forming step, the deposition time ranges from 100 s~3000 s, and preferably from 500 s~2000 s.

For a given period of electrolytic deposition, the lower the concentration of the electroplating solution, the thinner and more uniform the formed layer is and the fewer cracks generate in the layer. For a given coating thickness, the lower concentration of the electroplating solution, the longer deposition time is. At the $ZrO_2$ forming step, the concentration of $ZrO(NO_3)_2$ bath is in the range of 0.0001M~0.5M, and preferably from 0.001M~0.002M. At the HA forming step, the concentrations of $Ca(NO_3)_2 \cdot 4H_2O$ and $NH_4H_2PO$ in the mixed solution are respectively 0.02M~0.15M and 0.005M~0.5M, and preferably 0.04 M~0.1M and 0.02M~0.25M, depending on the deposition time.

In addition to the deposition, the drying and sintering are also crucial to the coating quality. If the coatings are not subject to slow drying such as air drying before sintered, a portion of moisture near the top of the coatings evaporates off while the remaining portion thereof is still inside the coatings, which results in crack due to non-uniform stress distribution. Thereby, the adhesion between the $ZrO_2$ and the substrate or the adhesion between the HA and $ZrO_2$ is deteriorated, even though the coatings may be peeled off to expose the substrate. In order to avoid such a problem, it is necessary to slowly dry the coated substrate before the sintering process. Furthermore, in order to prevent the moisture evaporates too quickly to generate cracks, the coated substrate is dried at constant temperature and humidity. The optimal drying temperature is 15~40° C. and the optimal relative humidity is more than 75%.

The dried substrate still contains a little moisture after slowly dried. Then, the substrate has to be further dried to thoroughly remove the moisture and thus complete a condensation reaction to form the $HA/ZrO_2$ complex coating.

According to TGA/DTA analysis, HA releases a lot of moisture at 200° C. and begins exothermic reaction at above 390° C. $ZrO_2$ colloids proceed vigorous exothermal reaction at about 300~350° C. and releases water of crystallization. In order to prevent large change in volume of the resulatnt complex coating, the sintering temperature is raised at stages, and the temperature is kept for a while between the temperature raising stages. The heating rate and cooling rate must be not high in order to prevent the adhesion of the complex coating from being deteriorated due to dismatch between thermal expansion coefficients of the HA and $ZrO_2$ layers.

Figure 2:
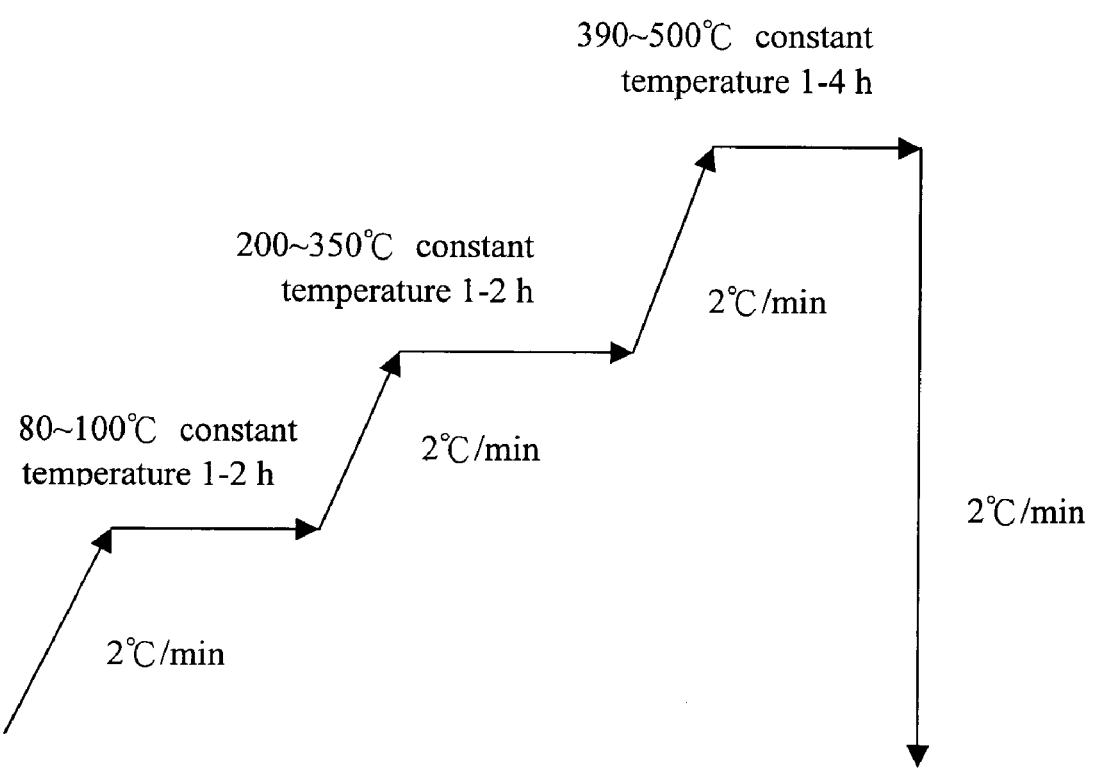
FIG. 2 is a schematic view of temperature change of a sintering process used in a process of forming HA/ZrO$_2$ complex coating according to one embodiment of the invention.

FIG. 2 illustrates the sintering process used in the invention. The sintering process includes a plurality of heating stages. In this embodiment, the sintering process includes sintering stage I) to stage VII).

Referring to FIG. 2, at stage I), the substrate is heated to about 80~100° C. at a rate of 2° C./min. At stage II), the substrate is sintered at about 80~100° C. for 1~2 hours. At stage III), the substrate is heated to about 200~350° C. at a rate of 2° C./min. At stage IV), the substrate is sintered at about 200~350° C. for 1~2 hours. At stage V), the substrate is heated to about 390~500° C. at a rate of 2° C./min. At stage VI), the substrate is sintered at about 390~500° C. for 1~2 hours. At stage VII), the substrate is cooled down from 390~500° C. to the initial temperature.

A pre-treatment can be further performed before the electrolytic deposition. The pre-treatment includes polishing and surface cleaning.

The deposition of the $HA/ZrO_2$ complex coating is achieved by using low concentration of plating solution and appropriate voltage. The $ZrO_2$ layer is formed as an interface during the formation of the HA layer to increase the bonding of the coated layers and the substrate and to increase the mechanical strength of the HA layer. The uniformity of the $ZrO_2$ and HA layers is determined by the electrical field distribution applied for electrolytic deposition. If the electrical field is uniformly distributed, the thickness of the coated layers is uniform.

Immediately after the electrolytic deposition of the $ZrO_2$ layer and the HA layer, HA crystals appear on the untreated complex coating. The HA crystals exhibit higher diffraction intensity and better adhesion to the metallic substrate after thermal treatment. Therefore, the $HA/ZrO_2$ complex coating protects the metallic substrate from being corroded or damaged while increases the bioactivity and mechanical strength.

EXAMPLE

A Co—Cr—Mo substrate is cut into a plurality of round specimens, each being 13 mm in diameter and 0.2 mm in thickness. The round specimens are respectively ground by using sand papers #240, #400, #600, #800, #1200 and #1500. Then, using 0.3 mm-sized alumna powders polishes these round specimens. After cleaned by detergents, the round specimens are placed into an ultrasonic vibrator for 10 min to further remove any stain or spot thereon. Then, the round specimens are rinsed by de-ioned water, and air dried.

Each round specimens is placed in the $ZrO(NO_3)_2$ bath to perform deposition of the $Zr(OH)_4$, with a platinum strip as an anode and the round specimen as a cathode. Then, the round specimens is moved to a mixed solution of $Ca(NO_3)_2 \cdot 4H_2O$ and $NH_4H_2PO_4$ from the $ZrO(NO_3)_2$ bath to perform the deposition of the HA layer. An optimal voltage is found along the critical voltage curve of the cathode polarization graph.

Then, the specimens are dried in an oven at 30° C. and relative humidity of 80%.

The round specimens s are respectively sintered at 80° C., 150° C., 350° C. and 500° C., each sintering duration at each temperature being about 1 hour. Then, the round specimens are subjected to an electrochemical polarization test and a TGA test. The round specimens are dipped in a Hank's solution to perform polarization cycling at 37° C. The result of polarization cycling is listed in Table 1.

TABLE 1

| Type of specimens | corrosion current density (nA/cm$^2$) | corrosion potential v.s. SCE (mV) |
|---|---|---|
| Uncoated specimen | 216.7 | −317.4 |
| HA/ZrO$_2$ complex layer coated specimen | 192.3 | −111.0 |

From Table 1, the corrosion electrical current used for the HA/ZrO$_2$ coated specimen is significantly improved compared to that used for non-HA/ZrO$_2$ coated specimen.

The specimen having a HA single layer and the specimen having a HA/ZrO$_2$ complex coating are subjected to a scratch test. The result is listed in Table 2.

TABLE 2

| Type of specimen | Maximum load (N) of the scratch test |
|---|---|
| HA single layer coated specimen | 2 |
| HA/ZrO$_2$ complex layer coated specimen | 16 |

From Table 2, the HA/ZrO$_2$ complex layer coated specimen having stands a load higher than the HA single layer coated specimen, showing the adhesion of the HA/ZrO$_2$ complex layer coated specimen being higher than that of the HA single layer coated specimen.

According to the experimental result, the HA/ZrO$_2$ complex layer electrolytic deposited specimen has significantly improved corrosion resistance and adhesion.

As described above, the HA/ZrO$_2$ complex coating of the invention, formed by the electrolytic deposition and the sintering process that stepwisely increases the sintering temperature, has improved adhesion and corrosion resistance. The sintering temperature is not higher than 500° C. According to the results of XRD, the HA/ZrO$_2$ complex coating does not contain other phases therein. The above electrolytic deposition and the sintering process are low-cost processes. Therefore, the formation of the HA/ZrO$_2$ complex coating with good adhesion and corrosion resistance is achieved by low production cost.

Furthermore, a thickness and topography of the HA/ZrO$_2$ complex coating is determined under the control of electrochemical and sintering parameters. The process of forming the HA/ZrO$_2$ complex coating according to the invention can be used to form the HA/ZrO$_2$ complex coating on a smooth, porous or other topographic metallic alloy.

It should be apparent to those skilled in the art that the above description is only illustrative of specific embodiments and examples of the invention. The invention should therefore cover various modifications and variations made to the herein-described structure and operations of the invention, provided they fall within the scope of the invention as defined in the following appended claims.

What is claimed is:

1. A process of forming a HA/ZrO$_2$ complex coating on a Co—Cr—Mo alloy substrate, the Co—Cr—Mo substrate being subject to an electrolytic deposition sequentially in a $ZrO(NO_3)_2$ bath and a mixed solution of $Ca(NO_3)_2 \cdot 4H_2O$ and $NH_4H_2PO_4$, and then the substrate being sintered to form the HA/ZrO$_2$ complex coating on the Co—Cr—Mo substrate.

2. The process of claim 1, wherein the electrolytic deposition of the Co—Cr—Mo substrate in the $ZrO(NO_3)_2$ bath forms a $Zr(OH)_4$ colloidal layer on the Co—Cr—Mo substrate.

3. The process of claim 1, wherein the electrolytic deposition of the Co—Cr—Mo substrate in the mixed solution of $Ca(NO_3)_2 \cdot 4H_2O$ and $NH_4H_2PO_4$ forms a $Ca_{10}(PO_4)_6(OH)_2$ layer on the $Zr(OH)_4$ colloidal layer.

4. The process of claim 1, wherein the substrate having the $Ca_{10}(PO_4)_6(OH)_2$ layer and the $Zr(OH)_4$ colloidal layer thereon is dried and sintered to form the HA/ZrO$_2$ complex coating.

5. The process of claim 1, wherein the concentration of the $ZrO(NO_3)_2$ bath is the range of 0.0001M~0.5M.

6. The process of claim 1, wherein the concentration of the $ZrO(NO_3)_2$ bath is the range of 0.001M~0.02M.

7. The process of claim 1, wherein the duration of electrolytic depositing the substrate in the $ZrO(NO_3)_2$ bath is about 150 s~about 3500 s.

8. The process of claim 1, wherein the duraiton of electrolytic depositing the substrate in the $ZrO(NO_3)_2$ bath is about 300 s~about 2000 s.

9. The process of claim 1, wherein the concentrations of $Ca(NO_3)_2 \cdot 4H_2O$ and $NH_4H_2PO_4$ in the mixed solution are respectively 0.02M~0.15M and 0.005M~0.5M.

10. The process of claim 1, wherein the concentrations of the $Ca(NO_3)_2 \cdot 4H_2O$ and $NH_4H_2PO_4$ in the mixed solution are respectively 0.04M~0.1M and 0.02M~0.25M.

11. The process of claim 1, wherein the duration of electrolytic depositing the substrate in the mixed solution of $Ca(NO_3)_2 \cdot 4H_2O$ and $NH_4H_2PO_4$ is about 100 s~3000 s.

12. The process of claim 1, wherein the duraiton of electrolytic depositing the substrate in the mixed solution of $Ca(NO_3)_2 \cdot 4H_2O$ and $NH_4H_2PO_4$ is about 500 s~2000 s.

13. The process of claim 1, wherein voltage used for electrolytic depositing the substrate in the $ZrO(NO_3)_2$ bath is about −0.6 V~−2.5 V.

14. The process of claim 1, wherein voltage used for electrolytic depositing the substrate in the $ZrO(NO_3)_2$ bath is about −0.75 V~1.1 V.

15. The process of claim 1, wherein voltage used for electrolytic depositing the substrate in the mixed solution of $Ca(NO_3)_2 \cdot 4H_2O$ and $NH_4H_2PO_4$ is about $-0.5$ V~$-3$V.

16. The process of claim 1, wherein voltage used for electrolytic depositing the substrate in the mixed solution of $Ca(NO_3)_2 \cdot 4H_2O$ and $NH_4H_2PO_4$ is about $-0.6$ V~$-1.4$ V.

17. The process of claim 1, wherein the substrate having the $Zr(OH)_4$ colloidal layer and the $Ca_{10}(PO_4)_6(OH)_2$ layer thereon is slowly dried at constant temperature and humidity before sintered.

18. The process of claim 1, wherein the substrate is further dried at temperature of about 15~40° C. and relative humidity of more than 75% before sintered.

19. The process of claim 1, wherein the sintering temperature is not high than 500° C.

20. The process of claim 1, wherein the sintering temperature is raised at stages, the temperature changing rate is not quick, and the temperature is kept for a while between two temperature changing stages.

21. The process of claim 20, wherein the temperature is raised at 2° C./min at each temperature changing stage.

22. A process of forming a $HA/ZrO_2$ complex coating on a Co—Cr—Mo alloy substrate, the Co—Cr—Mo substrate being subjected to an electrolytic deposition sequentially in a $ZrO(NO_3)_2$ bath and a mixed solution of $Ca(NO_3)_2 \cdot 4H_2O$ and $NH_4H_2PO_4$, then the substrate being slowly dried, and the substrate being sintered at a temperature not higher than 500° C. to form the $HA/ZrO_2$ complex coating on the Co—Cr—Mo substrate, wherein the sintering temperature is raised at several temperature stages.

23. The process of claim 22, wherein the electrolytic deposition of the Co—Cr—Mo substrate in the $ZrO(NO_3)_2$ bath forms a $Zr(OH)_4$ colloidal layer on the Co—Cr—Mo substrate.

24. The process of claim 22, wherein the electrolytic deposition of the Co—Cr—Mo substrate in the mixed solution of $Ca(NO_3)_2 \cdot 4H_2O$ and $NH_4H_2PO_4$ forms a $Ca_{10}(PO_4)_6(OH)_2$ layer on the $Zr(OH)_4$ colloidal layer.

25. The process of claim 22, wherein the substrate having the $Ca_{10}(PO_4)_6(OH)_2$ layer and the $Zr(OH)_4$ colloidal layer thereon is dried and sintered to form the $HA/ZrO_2$ complex coating.

26. The process of claim 22, wherein the concentration of the $ZrO(NO_3)_2$ bath is the range of 0.0001M~0.5M.

27. The process of claim 22, wherein the concentration of the $ZrO(NO_3)_2$ bath is the range of 0.001M~0.02M.

28. The process of claim 22, wherein the duration of electrolytic depositing the substrate in the $ZrO(NO_3)_2$ bath is about 150 s~about 3500 s.

29. The process of claim 22, wherein the duration of electrolytic depositing the substrate in the $ZrO(NO_3)_2$ bath is about 300 s~about 2000 s.

30. The process of claim 22, wherein the concentrations of $Ca(NO_3)_2 \cdot 4H_2O$ and $NH_4H_2PO_4$ in the mixed solution are respectively 0.02M~0.15M and 0.005M~0.5M.

31. The process of claim 22, wherein the concentrations of the $Ca(NO_3)_2 \cdot 4H_2O$ and $NH_4H_2PO_4$ in the mixed solution are respectively 0.04M~0.1M and 0.02M~0.25M.

32. The process of claim 22, wherein the duration of electrolytic depositing the substrate in the mixed solution of $Ca(NO_3)_2 \cdot 4H_2O$ and $NH_4H_2PO_4$ is about 100 s~3000 s.

33. The process of claim 22, wherein the duration of electrolytic depositing the substrate in the mixed solution of $Ca(NO_3)_2 \cdot 4H_2O$ and $NH_4H_2PO_4$ is about 500 s~2000 s.

34. The process of claim 22, wherein voltage used for electrolytic depositing the substrate in the $ZrO(NO_3)_2$ bath is about $-0.6$ V~$-2.5$ V.

35. The process of claim 22, wherein voltage used for electrolytic depositing the substrate in the $ZrO(NO_3)_2$ bath is about $-0.75$ V~$-1.1$ V.

36. The process of claim 22, wherein voltage used for electrolytic depositing the substrate in the mixed solution of $Ca(NO_3)_2 \cdot 4H_2O$ and $NH_4H_2PO_4$ is about $-0.5$ V~$-3$V.

37. The process of claim 22, wherein voltage used for electrolytic depositing the substrate in the mixed solution of $Ca(NO_3)_2 \cdot 4H_2O$ and $NH_4H_2PO_4$ is about $-0.6$ V~$-0.4$ V.

38. The process of claim 22, wherein the substrate having the $Zr(OH)_4$ colloidal layer and the $Ca_{10}(PO_4)_6(OH)_2$ layer thereon is slowly dried at constant temperature and humidity before sintered.

39. The process of claim 22, wherein the substrate is further dried at temperature of about 15~40° C. and relative humidity of more than 75% before sintered.

* * * * *